United States Patent
Barford

(10) Patent No.: US 6,738,450 B1
(45) Date of Patent: May 18, 2004

(54) SYSTEM AND METHOD FOR COST-EFFECTIVE CLASSIFICATION OF AN OBJECT UNDER INSPECTION

(75) Inventor: Lee A. Barford, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/316,299

(22) Filed: Dec. 10, 2002

(51) Int. Cl.$^7$ ............................................. G01N 23/02
(52) U.S. Cl. ................................... 378/58; 378/62
(58) Field of Search ........................... 378/51, 54, 58, 378/62

(56) References Cited

U.S. PATENT DOCUMENTS

| | | |
|---|---|---|
| 4,926,452 A | 5/1990 | Baker et al. |
| 5,081,656 A | 1/1992 | Baker et al. |
| 5,097,492 A | 3/1992 | Baker et al. |
| 5,199,054 A | 3/1993 | Adams et al. |
| 5,259,012 A | 11/1993 | Baker et al. |
| 5,291,535 A | 3/1994 | Baker et al. |
| 5,561,696 A | 10/1996 | Adams et al. |
| 5,583,904 A | 12/1996 | Adams |
| 5,621,811 A | 4/1997 | Roder et al. |
| 5,687,209 A | 11/1997 | Adams |
| 6,002,739 A | 12/1999 | Heumann |
| 6,178,223 B1 | 1/2001 | Solomon et al. |
| 6,201,850 B1 | 3/2001 | Heumann |
| 2002/0095259 A1 * | 7/2002 | Hood et al. ............ 702/19 |

OTHER PUBLICATIONS

U.S. patent application Ser. No. 10/106,435, Smith, filed Mar. 26, 2002.

Silverman, Bernard W., "Density Estimation for Statistics and Data analysis", Table of contents, Chapman and Hall, London, 1985.

Sivia, D.S., "Data Analysis: A Bayesian Tutorial", Chapter 4. Oxford University Press, 1996.

Gershenfeld, N. et al., "Cluster–weighted modelling for time–series analysis", Nature, vol. 397, 1999, pp. 329–332.

Fukinaga, Keinosuke, "Introduction to Statistical Pattern Recognition", Academic Press, 2nd Edition, 1990, pp. 51–58.

Gershenfeld, N., "The Nature of Mathematical Modeling", Cambridge Univ. Press, 1999, pp. 172–185.

Popat, K. et al., "Cluster Based Probability Model and Its Application to Image and Texture Processing", IEEE Trans. Image Processing, 6(2), 1997, pp. 268–284.

* cited by examiner

*Primary Examiner*—David V Bruce

(57) ABSTRACT

The system and method enable cost-effective classification of objects, such as solder joints, that are under inspection. A classifier is operable to receive a feature vector f of an object under inspection and compute a probability that such object is properly assigned membership in a first of a plurality of different classes. For instance, a "good" class may be available for objects that meet a pre-determined criteria, and a "bad" class for objects that do not meet such criteria. The classifier analyzes f to compute the probability that an object is properly classified as "good." Embodiments of the invention enable the classifier to be tuned as desired for a given inspection section for proper risk management. A cost variable is input to the classifier and used to determine whether, given the computed probability that an object is "good," it is cost-effective to classify the object as "good."

21 Claims, 7 Drawing Sheets

SYSTEM AND METHOD FOR COST-EFFECTIVE CLASSIFICATION OF AN OBJECT UNDER INSPECTION

TECHNICAL FIELD

The present invention relates in general to classification of objects under inspection, and more particularly to a system and method for cost-effective classification of an object, such as solder joints, in one of a plurality of different classes.

BACKGROUND OF THE INVENTION

A key challenge facing electronics manufacturers is quality analysis of their products. That is, electronics manufacturers typically want to ensure that their products are of high quality both structurally and functionally. Accordingly, certain techniques for testing the quality of electronic products have been developed. Considering the trend toward smaller components, increased manufacturing complexity, new packaging technologies, and higher functionality boards, new challenges continue to arise in quality testing of electronic products. Additionally, electronics manufacturers typically face extreme cost and time pressures such that it becomes important to implement a quality testing technique that does not substantially increase the cost and/or time associated with the manufacturing process. Preferably, the quality testing technique should aid the manufacturer in reducing the cost and/or time associated with the manufacturing process, e.g., by detecting defects in products as early as possible in the manufacturing process to enable timely correction of such defects and/or to avoid wasted time and expense in further manufacturing of a defected part.

One area in which quality analysis is often desired in electronic products is analysis of solder joints included therein. It is important for solder joints to be of an acceptable quality in electronic products to ensure that the soldered components are structurally and functionally sound. That is, it is important for a solder joint to be of good quality to ensure that the soldered component is securely coupled to the board in a structurally sound manner, and it is important for a solder joint to be of good quality to ensure that the soldered component is electrically coupled to the board in a manner that enables communication of electrical signals to/from the component through such solder joint so that the product can function as desired. As the complexity of electronic products increases, the number of solder joints present in such products tends to increase. For example, many high-complexity products have as many as 20,000 or 30,000 solder joints. A defect with any one of the solder joints in a product may result in the product being structurally and/or functionally unacceptable.

Thus, solder joints impact the structural and functional soundness of electronic products, and it is therefore typically desirable to test the quality of such solder joints to ensure that the products are of desired quality. Of course, it is also desirable to have a quality analysis technique that is reliable and does not substantially increase the cost and/or time involved in the manufacturing process. Automated image processing techniques have been used for analyzing the quality of solder joints. For example, automated optical inspection (AOI) and automated X-ray inspection (AXI) techniques have been developed and implemented for analyzing the quality of solder joints in electronic products. An example of an image processing solution for testing the quality of solder joints is provided in the SJ-50 automated optical inspection system commercially available from Agilent Technologies.

An example of a laminography system that may be utilized for electronics inspection is described further in U.S. Pat. No. 6,201,850 entitled "ENHANCED THICKNESS CALIBRATION AND SHADING CORRECTION FOR AUTOMATIC X-RAY INSPECTION", which is assigned to the assignee of this application and the disclosure of which is hereby incorporated herein by reference. Further examples of laminography systems that may be utilized for electronics inspection are described in the following patents: 1) U.S. Pat. No. 4,926,452 entitled "AUTOMATED LAMINOGRAPHY SYSTEM FOR INSPECTION of ELECTRONICS", issued to Baker et al.; 2) U.S. Pat. No. 5,097,492 entitled "AUTOMATED LAMINOGRAPHY SYSTEM FOR INSPECTION OF ELECTRONICS", issued to Baker et al.; 3) U.S. Pat. No. 5,081,656 entitled "AUTOMATED LAMINOGRAPHY SYSTEM FOR INSPECTION OF ELECTRONICS", issued to Baker et al.; 4) U.S. Pat. No. 5,291,535 entitled "METHOD AND APPARATUS FOR DETECTING EXCESS/INSUFFICIENT SOLDER DEFECTS", issued to Baker et al.; 5) U.S. Pat. No. 5,621,811 entitled "LEARNING METHOD AND APPARATUS FOR DETECTING AND CONTROLLING SOLDER DEFECTS", issued to Roder et al; 6) U.S. Pat. No. 5,561,696 "METHOD & APPARATUS FOR INSPECTING ELECTRICAL CONNECTIONS", issued to Adams et al.; 7) U.S. Pat. No. 5,199,054 entitled "METHOD AND APPARATUS FOR HIGH RESOLUTION INSPECTION OF ELECTRONIC ITEMS", issued to Adams et al.; 8) U.S. Pat. No. 5,259,012 entitled "LAMINOGRAPHY SYSTEM AND METHOD WITH ELECTROMAGNETICALLY DIRECTED MULTIPATH RADIATION SOURCE", issued to Baker et al.; 9) U.S. Pat. No. 5,583,904 entitled "CONTINUOUS LINEAR SCAN LAMINOGRAPHY SYSTEM AND METHOD", issued to Adams; and 10) U.S. Pat. No. 5,687,209 entitled "AUTOMATIC WARP COMPENSATION FOR LAMINOGRAPHIC CIRCUIT BOARD INSPECTION", issued to Adams. The entirety of each of the above referenced patents is hereby incorporated herein by reference.

Another imaging technique used in inspection systems is known as tomosynthesis. Tomosynthesis is an approximation to laminography in which multiple projections (or views) are acquired and combined. As the number of views becomes large, the resulting combined image generally becomes identical to that obtained using laminography with the same geometry. Tomosynthesis may be performed as an analog method, for example, by superimposing sheets of exposed film. Tomosynthesis may, instead, be performed as a digital method. In digital tomosynthesis, the individual views are divided into pixels, and digitized and combined via computer software. Three-dimensional computed tomography, such as "cone-beam tomography" for example, is another well-known image processing technique that may be used in inspection of an object. Example tomosynthesis (or tomography) systems that have been proposed for use in industrial inspection systems include, as examples, those disclosed in U.S. Pat. No. 6,002,739 entitled "COMPUTED TOMOGRAPHY WITH ITERATIVE RECONSTRUCTION OF THIN CROSS-SECTIONAL PLANES" and U.S. Patent No. 6,178,223 entitled "IMAGE RECONSTRUCTION METHOD AND APPARATUS," the disclosures of which are hereby incorporated herein by reference in their entirety.

In addition to image processing techniques, various other tests of an electronic product, such as in-circuit tests (ICTs) and function tests (FTs) may be performed for testing the functionality of the electronic product. A common test strategy for high-complexity printed circuit boards (PCBs) is to use a combination of AXI, ICT, and FT in which AXI tests the structural integrity of the solder joints, ICT tests the electrical integrity of the components and PCB, and FT verifies the PCB's performance characteristics. On complex boards, typically about 80 to 90 percent of all defects found are structural or process defects. AXI testing generally provides about 95 percent coverage of the structural defects. Therefore, it is generally advantageous to use AXI before ICT and FT testing of an electronic product as filtering out of those defective products detected with AXI significantly reduces the number of defects arising during ICT and FT. In addition, AXI typically pinpoints the exact location of the defects (e.g., identifies the specific solder joint that is defective), thus enabling the defect to be repaired in a timely and cost-effective manner before undergoing ICT and FT testing.

Generally, an automated inspection system classifies objects (e.g., solder joints) based on measurements taken of the object being inspected. For example, in a manufacturing inspection system, a customary goal is to determine whether a given object of manufacture is either "good" or "bad" (i.e., belongs to a class of good objects or a class of bad objects). Unfortunately, due to statistical variations in measured characteristics of the inspected objects and/or statistical errors in the measurements themselves, the determination of class membership usually is not deterministic but instead is made according to probability theory. In other words, the determination establishes a likelihood or probability that a given object is a member of a particular class or category. Moreover, in many practical cases no single measurement can be used to reliably perform the categorization. Instead, multiple measurements are often required. The measurements and/or combinations of the measurements can be thought of as "features" (or "parameters") of the object. For example, various features of a solder joint may be measured by an inspection system, such as length, width, thickness, curvature, relative opacity, and similar values of the solder joint. The object features are compared to sets of representative features for each of the possible groups (or classes) and a determination is made based on an aggregate of the comparison results. Thus, the classification problem is more correctly termed an estimation problem in which the probability of membership of the object in a particular group or class is estimated based on the features of the object. The branch of statistics that deals with the problem of classifying or estimating class membership based on features derived from multiple measurements is known as multivariate analysis or multivariate estimation.

Image processing of solder joints may enable a variety of parameters of a solder joint to be measured. For instance, a solder joint may be imaged, and such image may be processed to determine such parameters as length, width, thickness, curvature, relative opacity, and similar values of the solder joint. As an example, the thickness of solder material (which is typically a combination of lead and tin) may be inspected by an automated inspection system through analysis of X-ray image(s) of the solder material. In an X-ray image of solder material, there is a relationship between the intensities comprising the X-ray image and the thicknesses of the solder material forming the X-ray image. Typically, the image intensity increases from values corresponding to lighter shades of gray (white) to values corresponding to darker shades of gray (black) as the thickness of the solder material increases. That is, the image of a thin section of solder will have a gray level that is less than the gray level of the image of a thicker section of solder. The image of the thin section will appear to be a lighter shade of gray than the image of the thicker section. This convention is typically used in electronic image representation of X-ray images, however, the opposite convention may also be used, i.e., where the image of a thin section of solder has a gray level that is greater than the gray level of the image of a thicker section of solder. The latter convention has traditionally been followed in film radiography where the X-ray images are recorded on X-ray film.

The various parameters (or "features") determined for a solder joint may then be evaluated to determine whether the solder joint is acceptable. It should be understood that there may exist a range of parametric values that define a solder joint of acceptable quality. Accordingly, an automated technique may be implemented for evaluating the determined parameters of a solder joint to determine whether the solder joint is of acceptable quality.

Traditional image processing techniques rely on users (technicians) to define the parameter boundaries for acceptable and unacceptable solder joints. Such boundaries are typically defined in a rigid manner in which a single, constant upper and lower boundary value may be defined for each parameter (e.g., length, thickness, etc.). For instance, a user typically defines upper and lower boundary values for each parameter, and a solder joint is evaluated to determine whether each of its parameters falls within its respective boundary. If one parameter is outside of its defined boundary, then the solder joint is detected as being unacceptable irrespective of the value of the remaining parameters.

That is, in traditional image processing techniques a user defines a given boundary for a parameter that is used in evaluating the acceptability of the solder joint irrespective of the other parameter values. In this manner, assuming that each parameter is assigned an axis in "N" dimension space (wherein "N" corresponds to the number of parameters being evaluated), a user essentially defines a rectangular-shaped region of acceptable solder joints by assigning a constant upper and lower boundary to each parameter (i.e., an upper and lower boundary for a parameter that each remain constant irrespective of the values of the other parameters). For instance, assuming that 3 parameter values are analyzed for a solder joint (although typically many more parameters are included in the analysis), a three-dimensional ("3D") graph may be formed in which each axis of the graph corresponds to one of the 3 parameters. A technician may assign boundary values (e.g., upper and lower boundary values) to each of the parameters, thus essentially defining a rectangular-shaped region (i.e., a box) in the 3D space of acceptable solder joints. That is, the boundary values assigned to each parameter remain constant irrespective of the values of the other parameters, thus resulting in a rectangular-shaped region (or box) in which acceptable parameter values reside.

However, traditional automated solder joint quality analysis techniques have several disadvantages. First, such techniques are often inaccurate in classifying a solder joint. Second, it is typically undesirably time consuming to define a boundary region that defines acceptable solder joints. Third, because the techniques depend heavily on individual technicians for defining the test limits (boundary regions) to be used for a given analysis, the results are typically not uniform or repeatable from test to test. Finally, the construction of such automated testing techniques is further complicated by consideration of risk management. For instance, the cost of a false accept and of a false reject of a solder joint are not necessarily the same for a given product, and traditional classification techniques do not readily allow for such risk management (or cost considerations) to be employed in the quality analysis process.

More recently, an automated inspection technique using image processing as described hereafter has been implemented in such systems as Agilent's SJ-50 joint inspection system. According to this more recent inspection technique, an inspection system uses training data to train the inspection system to correctly classify an object under inspection. For instance, a feature vector f for an object under inspection may be input to the inspection system, and the inspection system compares that feature vector f to its stored training data to determine the best classification of the object under inspection. This inspection technique improves on the traditional inspection techniques in that it does not require a user to select thresholds (or boundaries) for each parameter. However, this inspection technique still has several disadvantages. First the accuracy of the k nearest neighbors method is sensitive to measurement noise in the feature vector f. Additionally, the accuracy of the k nearest neighbors method is sensitive to elements of f that have low power for distinguishing between "good" and "bad" joints compared to elements of f. Further, this inspection technique does not allow for consideration of risk management. For instance, as described above, the cost of a false accept and of a false reject of a solder joint are not necessarily the same for a given product. This inspection technique does not take into account the relative cost of deciding that a good joint is bad ("false fail") versus deciding that a bad joint is good ("false accept").

Automated inspection techniques of the prior art have failed to provide a mechanism to allow a user to specify risk management variables and have failed to take such risk management concerns into account when classifying an object under inspection. That is, the cost associated with incorrectly classifying an object is not taken into consideration by automated inspection systems of the prior art when classifying an object under inspection.

BRIEF SUMMARY OF THE INVENTION

The present invention is directed to a system and method which enable cost-effective classification of objects, such as solder joints, that are under inspection. More specifically, embodiments of the present invention provide a classifier that is operable to receive a feature vector f (which may be formed from measurements of various features of an object) of an object under inspection and compute a probability that such object is properly assigned membership in a first of a plurality of different classes. For instance, a "good" class may be available for objects that meet a pre-determined criteria, and a "bad" class may be available for objects that do not meet the pre-determined criteria. The classifier may analyze the feature vector f of an object to compute the probability that such object is properly classified as "good." Further, embodiments of the present invention enable the classifier to be tuned as desired for a given inspection session in order to take into consideration risk management concerns. For instance, as described above, for a given inspection session (e.g., the inspection of a particular product) a cost may exist for incorrectly classifying a bad object as "good." Embodiments of the present invention enable a cost variable to be input to the classifier, and the classifier uses such cost variable to determine whether, given the computed probability that an object is correctly classified as "good," it is cost-effective to classify the object as "good." Accordingly, if risk management concerns in a first inspection process for inspecting a given object differ from risk management concerns of a second inspection process for inspecting the given object, a common classifier for the given object may be used in both inspection processes but a different cost variable may be utilized for each process to tune the classifier for cost-effective classification in each process.

In accordance with one embodiment of the present invention, a method is provided for classifying an object as being a member of one of a plurality of classes. The method comprises computing a probability that an object under inspection is properly assigned membership in a first of a plurality of classes, and using a cost variable to determine whether it is cost-effective to assign the object to the first class given the computed probability. For example, the plurality of classes may comprise a "good" class for objects that meet a predefined criteria and a "bad" class for objects that do not meet the pre-defined criteria. The cost variable may, for example, comprise a variable $K=C_{GB}/C_{BG}$, wherein $C_{GB}$ is a cost associated with incorrectly classifying a good object as bad and $C_{BG}$ is a cost associated with incorrectly classifying a bad object as good. An example of an object that may be under inspection is a solder joint.

In accordance with another embodiment of the present invention, a method for classifying an object under inspection is provided. The method comprises inputting a feature vector for an object under inspection to a classifier for the object, and inputting a cost variable to the classifier that specifies a cost associated with incorrectly classifying the object under inspection in a first of a plurality of classes. The classifier uses the feature vector to compute a probability that the object under inspection is properly assigned membership in the first of a plurality of classes. And, the classifier uses the cost variable to determine whether it is cost-effective to assign the object to the first of the plurality of classes given the computed probability.

In accordance with another embodiment of the present invention, a method for inspecting an object is provided that comprises constructing a classifier for a first type of object. The classifier is operable to compute for an object of such first type that is under inspection a probability that such object under inspection is properly assigned membership in a first of a plurality of different classes. The method further comprises inputting a cost variable to the classifier to tune the classifier for cost-effective classification of the object under inspection.

In accordance with still another embodiment of the present invention, a system for classifying an object under inspection is provided. The system comprises at least one processor, and computer-executable code stored to a computer-readable medium, wherein such computer-executable code is executable by the at least one processor. The computer-executable code is executable to receive a feature vector for an object under inspection, and receive a cost variable that specifies a cost associated with incorrectly classifying the object under inspection. The computer-executable code is also executable to use the feature vector to compute, for each of a plurality of classes, a probability that the object under inspection is properly assigned membership in the respective class, and use the cost variable to determine the most cost-effective one of the plurality of classes to which to assign the object given the computed probability of each of the plurality of classes. In certain implementations, the computer-executable code executable to use the cost variable to determine the most cost-effective one of the plurality of classes comprises code executable to use the cost variable to compute, for each of the plurality of different classes, a cost associated with assigning the object under inspection to the respective class based at least in part on the computed probability that such object is properly assigned membership in the respective class, and code executable to determine the least costly one of the plurality of different classes to which to assign the object under inspection.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
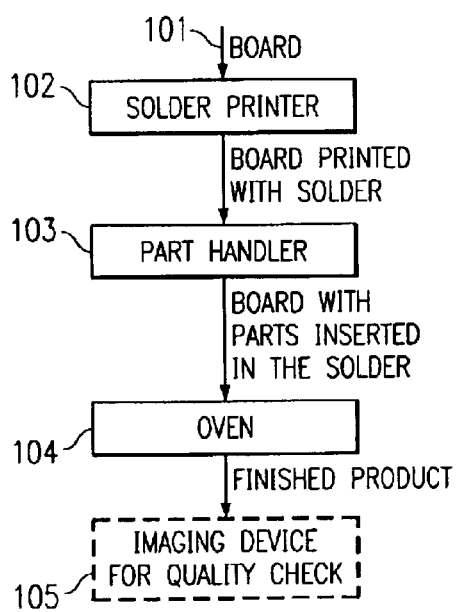
FIG. 1 shows an example process flow diagram for manufacturing and testing solder joints in accordance with techniques of the existing art.

In view of the above, automated procedures are implemented in the existing art for classifying objects, such as solder joints. For instance, image processing techniques may be used for generating a feature vector f for an object from one or more images of such object, and the feature vector f may then be analyzed by a classifier to determine the proper classification of the object. For example, an automated procedure may be implemented for analyzing the quality of a solder joint by using a set of feature measurements (referred to collectively herein as a feature vector f) extracted from an image of the solder joint to determine whether the joint is classified as "good" or "bad". The values within f are typically determined by software that locates certain image features and estimates parametric values of the solder joint's features, such as length, width, thickness, curvature, relative opacity, and similar values well-known to those skilled in the art of image processing. Whether an object is classified as "good" or "bad" may depend on whether the object meets a pre-defined criteria. For instance, a solder joint may be classified as "good" if it is determined from its feature vector f that it is of sufficient strength, thickness, etc. For classification of other objects, various other pre-defined criteria may be used, and one of ordinary skill in the art would be able to determine appropriate classification criteria to be implemented for a given inspection system without undue experimentation.

Image processing techniques may be used to acquire parameter (or "feature") measurements for a solder joint, and such measurements may be analyzed to determine whether the solder joint is classified as a "good" or a "bad" joint. That is, automated inspection techniques may perform object classification or identification using multivariate estimation. As described further below, object classification may be performed through use of measurements of an unknown object (e.g., solder joint) and/or measurements extracted from an image of the unknown object. The measurements and linear combinations of the measurements are features of the object being classified, such as length, width, thickness, etc. of the object under inspection. The features are used to classify the unknown object as being a member in one of several classes or categories of objects (e.g., "good" or "bad"). The classes are preferably defined by features in a training set of known objects.

Embodiments of the present invention provide a technique for including risk management valuations into the object classification process. As described above, classification techniques estimate the probability of an object being a member in a particular group or class based on the features of the object. For instance, solder joints may be inspected and classified by an automated inspection system as either "good" or "bad" based on the solder joints' features. Depending on the product being manufactured, the cost of incorrectly classifying an object may vary. Further, the cost associated with incorrectly classifying an object within one class may differ from the costs of incorrectly classifying the object within another class. For instance, assume that an automated inspection system inspects solder joints and classifies the solder joints as either "good" (i.e., of acceptable quality) or "bad" (i.e., of unacceptable quality); the costs associated with incorrectly classifying the solder joint may vary depending on the product in which the solder joints are included. Further, the costs of incorrectly classifying a truly bad solder joint as being "good" may be different than the costs of incorrectly classifying a truly good solder joint as being "bad."

Automated inspection techniques of the prior art have failed to provide a mechanism to allow a user to specify such risk management variables and have failed to take such risk management concerns into account when classifying an object under inspection. That is, the cost associated with incorrectly classifying an object is not taken into consideration by automated inspection systems of the prior art when classifying an object under inspection. As described further below, embodiments of the present invention provide a system and method for classifying an object under inspection that is capable of taking risk management concerns into account. For instance, in a preferred embodiment of the present invention a user may specify a cost variable "K" associated with incorrectly classifying the object (e.g., the cost of an incorrect "bad" classification versus an incorrect "good" classification), and the automated inspection system uses such cost variable when classifying the object. Embodiments of the present invention are useful in a wide range of applications, including but not limited to, computer vision, automated inspection systems, and related image processing.

As described further below, in a preferred embodiment, training data is used to construct a classifier that is operable to determine (estimate) the probability that an object under inspection is properly included within a given class. That is, the classifier is operable to determine, for a given feature vector f of an object under inspection, the probability that the object is properly classified in each of a plurality of different classes. For instance, assuming that a class of "good" and a class of "bad" are available, based on a feature vector f received for an object under inspection, the classifier may determine the probability that such object is properly classified as "good" and may also determine the probability that such object is properly classified as "bad". Any technique now known or later discovered for constructing such a classifier is intended to be within the scope of the present invention, including but not limited to the example construction techniques described herein below.

Embodiments of the present invention enable a cost variable "K" to be implemented that specifies a relative cost of incorrectly classifying an object within each of the available classes. For instance, again assuming that a class of "good" and a class of "bad" are available, a cost variable "K" may be implemented (for the type of object under inspection) that indicates the relative cost of incorrectly classifying the object under inspection as "good" and the relative cost of incorrectly classifying the object under inspection as "bad." Such cost variable may then be used in evaluating the probability determined by the classifier that an object under inspection is properly assigned to a given class to determine the most cost-effective classification of the object. Accordingly, a user-friendly technique for incorporating risk management concerns into the classification process is provided.

FIG. 1 shows an example process flow diagram for manufacturing and testing solder joints in accordance with techniques of the existing art. In the example of FIG. 1, a printed circuit board (PCB) 101 is input to a "solder printer" device 102, which automatically applies solder to PCB 101. Typically, the solder used in solder printer 102 includes additives that work to maintain the solder viscous (e.g., to maintain the solder as a "gooey" substance). The solder printer 102 spreads the viscous solder over the PCB 101, and the solder collects in various holes of the PCB 101 in which electronic components are to be inserted. Thus, solder printer 102 outputs the PCB 101 that is printed with solder. Thereafter, the board is input to a part handler 103 that is operable to handle electronic components (e.g., chips) and arrange such components on the board. That is, part handler 103 is operable to automatically insert pins of a component into the appropriate holes of board 101. Because solder has been printed onto the board, the components are inserted into such solder by part handler 103. Thus, part handler 103 outputs the PCB with the electrical components arranged thereon (with the component's pins inserted into the solder on the PCB).

The board is then input to an oven 104, which heats the solder and evaporates the additives that maintain the solder viscous (such that the solder can harden or solidify when it cools). After the product comes out of oven 104, it is allowed to cool and the solder joints formed to couple the electronic components to the PCB solidify, thus resulting in the finished product. The finished PCB may then be input to an imaging device 105 (e.g., an optical or X-ray imaging device, such as the laminography system disclosed in U.S. Pat. No. 6,201,850 entitled "ENHANCED THICKNESS CALIBRATION AND SHADING CORRECTION FOR AUTOMATIC X-RAY INSPECTION") or a tomography system as disclosed in U.S. Pat. No. 6,002,739 entitled "COMPUTED TOMOGRAPHY WITH ITERATIVE RECONSTRUCTION OF THIN CROSS-SECTIONAL PLANES" or U.S. Pat. No. 6,178,223 entitled "IMAGE RECONSTRUCTION METHOD AND APPARATUS" as examples, which may acquire and process an image of the solder joints to measure various parameters of such solder joints, such as length, width, thickness, curvature, relative opacity, etc.

As described above, in traditional automated inspection systems, a boundary (or test limit) may be specified for each parameter of the solder joints, which may be used during the quality analysis to determine whether the solder joint is of acceptable quality. In traditional automated testing procedures, a technician is relied upon to choose test limits, i.e., lower and upper bounds of a solder joint's feature vector f, written l and u respectively. In such an automated scheme, a solder joint is designated "good" if $l \leq f \leq u$ and "bad" otherwise. Inequalities among vectors are to be interpreted componentwise. That is, $a \leq b$ if and only if $a_i \leq b_i$ for every i.

Figure 2A:
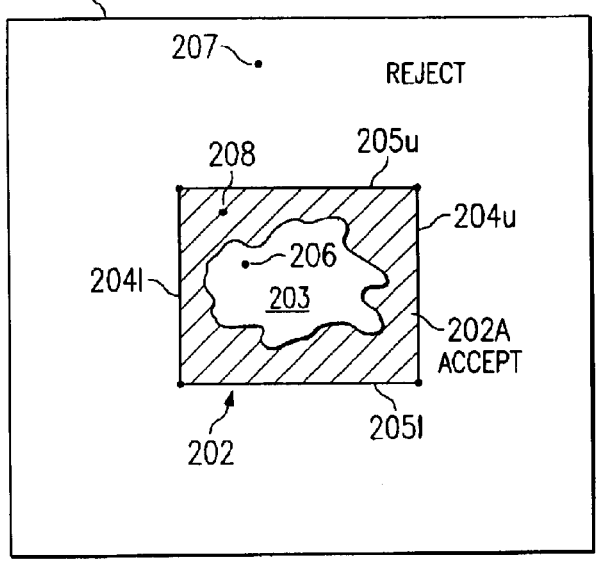
FIGS. 2A–2B show an example of defining upper and lower bounds for inspecting a solder joint in accordance with traditional automated inspection techniques.

As mentioned above, this results in a rectangular-shaped region of "good" solder joints being formed by a user specifying such upper and lower bounds for the parameters. For instance, turning to FIGS. 2A–2B an example of defining such upper and lower bounds in accordance with traditional automated inspection techniques is illustrated. In the example of FIG. 2A, feature space 201 represents all possible values of a feature vector f for a solder joint. Within such feature space 201, a region 202 of feature vector values is defined that the inspection system is to identify as being acceptable. More specifically, a technician defines upper and lower bounds for each of a plurality of different parameters that make up the feature vector f . For instance, in the example of FIG. 2A, a lower boundary 204l and an upper boundary 204u are defined for a first parameter, and a lower boundary 205l and an upper boundary 205u are defined for a second parameter. During the quality analysis process, a solder joint is considered "good" if and only if it lies within the rectangular-shaped region 202 bound by the specified test limits. While FIG. 2A provides a two-dimensional example (i.e., two parameters are used for measuring the quality of a solder joint) for ease of illustration, such quality analysis usually utilizes many more parameters (resulting in "N"-dimension space for graphically representing the acceptable region).

Accordingly, a user defines a constant upper boundary and constant lower boundary value for each parameter used in the analysis, and a solder joint is evaluated to determine whether each of its parameters falls within its respective boundary. If one parameter is outside of its defined boundary, then the solder joint is detected as being unacceptable irrespective of the value of the remaining parameter values. In reality, the region of acceptable solder joints typically does not correspond to such a rigid, rectangular-shaped region because of interdependencies between the various parameters. That is, there is correlation between elements of the feature vector f such that the value of one parameter may effect the range of acceptable values of other parameters. For instance, the true region 203 of acceptable solder joints is neither rectangular nor aligned with the axes of such feature space.

As shown in the example of FIG. 2A, acceptable region 202 is defined to encompass all of the truly acceptable solder joints of region 203. For instance, a first value 206 of feature vector f that maps within region 203 (and thus indicates a truly acceptable solder joint) is determined by the testing procedure as being indicative of an acceptable solder joint because it is within the defined acceptable region 202. Likewise, a second value 207 of feature vector f that maps outside of the defined acceptable region 202 is properly determined by the testing procedure as being indicative of an unacceptable solder joint because it is not within the truly acceptable region 203. However, the defined acceptable region 202 is over-inclusive in this example in that it includes the values within shaded region 202A, which are values of feature vector f that do not map within the truly acceptable region 203. For instance, a third value 208 of feature vector f that maps outside of region 203 (and thus is an unacceptable solder joint) is determined by the testing procedure as being indicative of an acceptable solder joint because it is within the defined acceptable region 202.

Figure 2B:
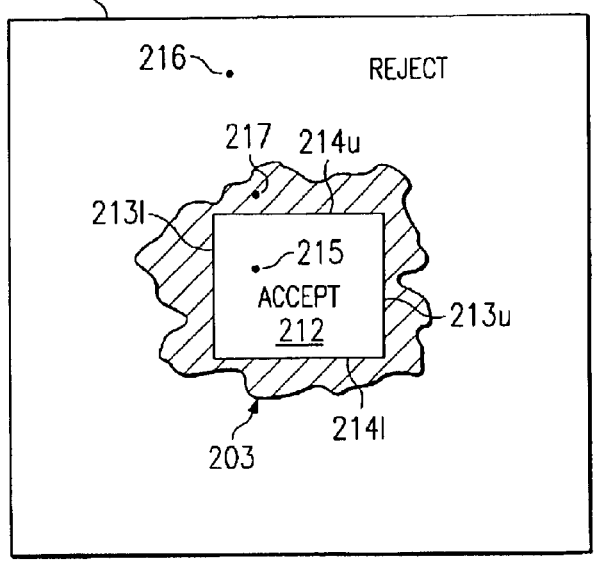

In the example of FIG. 2B, region 212 of feature vector values that the inspection system is to identify as being acceptable is defined within feature space 201. More specifically, a technician defines upper and lower bounds for each of a plurality of different parameters that make up the feature vector f. For instance, in the example of FIG. 2B, a lower boundary 213*l* and an upper boundary 213*u* are defined for a first parameter, and a lower boundary 214*l* and an upper boundary 214*u* are defined for a second parameter. As explained above with FIG. 2A, during the quality analysis process, a solder joint is considered "good" if and only if it lies within the rectangular-shaped region 212 bound by the specified test limits. While FIG. 2B provides a two-dimensional example (i.e., two parameters are used for measuring the quality of a solder joint) for ease of illustration, such quality analysis usually utilizes many more parameters (resulting in "N"-dimension space for graphically representing the acceptable region).

As shown in the example of FIG. 2B, acceptable region 212 is under-inclusive in that it fails to encompass all of the truly acceptable solder joints of region 203. For instance, a first value 215 of feature vector f that maps within region 212 is properly determined by the inspection system as being indicative of an acceptable solder joint because it is within the truly acceptable region 203. Likewise, a second value 216 of feature vector f that maps outside of the defined acceptable region 212 is properly determined by the inspection system as being indicative of an unacceptable solder joint because it is not within the truly acceptable region 203. However, the defined acceptable region 212 is under-inclusive in this example in that it excludes the values within shaded region 203A, which are values of feature vector f that map within the truly acceptable region 203. For instance, a third value 217 of feature vector f that maps within the acceptable region 203 (and thus is an acceptable solder joint) is determined by the inspection system as being indicative of an unacceptable solder joint because it is outside of-the defined acceptable region 212.

In view of the above, traditional automated solder joint quality analysis techniques have several disadvantages. First, as described in greater detail above, such techniques are generally inaccurate in classifying objects under inspection. In order to classify solder joints in traditional testing techniques, a set of test limits (or parameter boundaries) that approximates a good separator of acceptable and unacceptable solder joints must be determined manually by a technician. It is known that this approximation is typically quite poor. For example, traditional techniques generally establish a constant upper and lower boundary for each parameter of an object. However, there is generally correlation between the various different parameters of an object under inspection, such as a solder joint. That is, the value of one parameter may effect the range of acceptable values of other parameters. Thus, the region of feature space occupied by acceptable solder joints is neither rectangular nor aligned with the axes of such space. Because the actual boundary between acceptable and unacceptable solder joints does not follow a rigid, rectangular-shaped pattern (e.g., because the range of acceptable values for a given parameter may vary depending on the values of other parameters), the boundaries implemented in a testing system are generally either too small (thus causing certain acceptable joints to be rejected) or too large (thus causing certain unacceptable joints to be accepted). In traditional inspection techniques, false accepts (i.e., the test indicating that an unacceptable solder joint is acceptable) result when the unacceptable (or "bad") region encroaches on the rectangular-shaped region in the feature space accepted by the testing method. That is, if the rectangular-shaped boundary is too large, then it may encompass unacceptable solder joints. Similarly, false rejects (i.e., the test indicating that an acceptable solder joint is unacceptable) occur when the acceptable (or "good") region lies outside the defined rectangular box. That is, if the rectangular-shaped boundary is too small, then it may fail to encompass all acceptable solder joints.

Second, it is undesirably time consuming to create the region to define the acceptable solder joints. That is, technicians spend considerable time attempting to find an adequate tradeoff between false accepts and-false rejects by manipulating the test limits. Since there are typically more than 3 parameters used in analyzing solder joint quality, it is typically not feasible for a technician to visualize the relationships between the "good" and "bad" regions and proposed test limits. Accordingly, because it is difficult for the technicians to visualize (or understand) the relationships between the various parameters, it is difficult for the technicians to develop reliable test limits that are neither over-inclusive (include bad solder joints along with good solder joints) nor under-inclusive (fail to recognize all of the good solder joints).

Third, because the techniques depend heavily on individual technicians for defining the test limits to be used for a given analysis, the results are typically not uniform or repeatable from test to test. Different technicians may produce wildly different test limits. Furthermore, similarly trained technicians have a dramatically different ability to produce test limit settings that are adequate.

Finally, the construction of such automated testing techniques is further complicated by consideration of risk management. For instance, the cost of a false accept and of a false reject of a solder joint are not necessarily the same for a given product. This is because unnecessary rework may not cost the same as producing a product of less-than-desired quality. These costs in turn reflect the cost and quality requirements of the product. For example, a product that is destined for a satellite that is to be launched into outer space and will be very difficult and expensive to repair/replace has a very different risk associated with it than does a consumer product, such as a transistor radio, that is to be sold at a retail store. Accordingly, it may be desirable to have much greater assurance in the quality of solder joints in the product destined for the satellite than may be required for the consumer product destined for the retailer. In principle, with traditional automated testing techniques of the existing art, the test limits may be adjusted by technicians to reflect these tradeoffs. That is, a technician may take into consideration the risks associated with incorrectly classifying a bad solder joint as good (and vice-versa) for the particular product under study when defining the test limits (or parameter boundaries) to be used in the quality analysis. However, attempting to take these further factors into consideration exacerbates the above-described difficulty in having a technician define the parameter boundaries by adding yet another consideration that must be made in selecting such boundaries.

Figure 3:
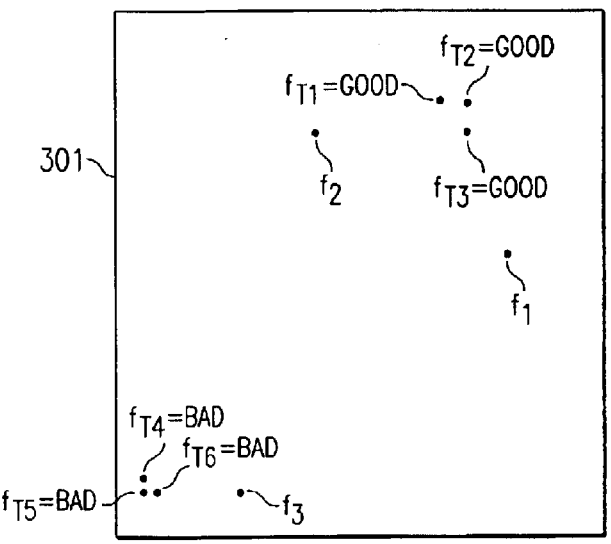
FIG. 3 shows an example of a more recent automated inspection technique that uses training data to construct a classifier that may then be used to evaluate a feature vector f and determine the probability that an object having such feature vector f is properly included within a given class.

More recently, automated inspection techniques have been developed that use training data to construct a classifier that may then be used to evaluate a feature vector f and determine the probability that an object having such feature vector f is properly included within a given class. For instance, a classifier may be constructed to determine from a received feature vector f of a solder joint under inspection, the probability that such solder joint is properly classified as "good" and the probability that such solder joint is properly classified as "bad." An example of this more recent inspection technique is shown in FIG. 3. As shown, an inspection system is first input a set of solder joints (e.g., on circuit boards) of a given type (e.g., ball grid arrays, etc.) that are known to be good and a set of solder joints that are known to be bad in order to train the inspection system to recognize good and bad joints of this type. For instance, for a given type of solder joint, a predetermined number (e.g., 6) of such solder joints are first run through the automated inspection system for setting the inspection system up for inspecting this type of joint. Of the solder joints input for the setup process, a predetermined number (e.g., 3) are known (e.g., through manual inspection by a technician and/or other testing thereof) to be good and a predetermined number (e.g., 3) are known to be bad. The inspection system measures and stores all of the feature vectors (parameters) for all of the joints used for setup, and the inspection system labels whether each joint was "good" or "bad."

For instance, in the example of FIG. 3, six solder joints are used for training the inspection system, three of which are known to be good and three of which are known to be bad. The inspection system analyzes the three good joints and determines training feature vectors $f_{T1}$, $f_{T2}$, and $f_{T3}$ for such joints, and the inspection system assigns a label of "good" to those training feature vectors. Training feature vectors $f_{T1}$, $f_{T2}$, and $f_{T3}$ are shown in FIG. 3 as being mapped within feature space 301, which represents all possible values of a feature vector f for a solder joint. The inspection system also analyzes the three bad joints and determines training feature vectors $f_{T4}$, $f_{T5}$, and $f_{T6}$ for such joints, and the inspection system assigns a label of "bad" to those training feature vectors. Training feature vectors $f_{T4}$, $f_{T5}$, and $f_{T6}$ are also shown in FIG. 3 as being mapped within feature space 301.

For the purposes of the discussion herein, the term "feature space" refers to a multidimensional space or volume that contains all of the measurement data that can result from a set of measurements taken for a set of objects (e.g., solder joints) being classified. For example, if five physical measurements, such as length, width, color, density, and volume, were taken, the feature space could be a 5-dimensional space having one axis for each feature. Within the feature space, individual measurements are represented as points having locations defined by coordinates associated with a particular coordinate system of the feature space. Alternatively, points in this space may be specified relative to a different or transformed coordinate system. A transformed coordinate system is one that is shifted, stretched, and/or rotated relative to the original coordinate system. Unit vectors along the axes of the new transformed coordinate system form a new basis of the measurement space. In addition, the feature space can contain linear combinations of measurements. The set of measurements taken for a given object and their linear combinations are said to be in the feature space and the feature space spans the total range of possible features. Measurements are either actual measurements of physical parameters associated with the object or derived parameters that are inferred from physical measurements or other sources.

The method of classification uses a so-called training set of measurement or feature data taken from a set of known objects, such as training feature vectors $f_{T1}$–$f_{T6}$ shown in FIG. 3. A known object is one whose group or class membership is known a priori. Once established, the training data set serves as a basis or template against which the features of an unknown object (e.g., a solder joint under inspection) are compared in an attempt to classify the object. The training set establishes the classes to which the unknown object is assigned. For instance, as with the example of FIG. 3, in automated solder joint inspection there may be two classes established, "good solder joints" and "bad solder joints." The training set contains examples of both good joints and bad joints and measurements of these known good joints and known bad joints are used to create the training set of feature data (e.g., $f_{T1}$–$f_{T6}$ of FIG. 3). Preferably, the training set contains examples of objects that span the classes or at least represent a good statistical sample of the classes. Determining a quantity of objects that make up a good statistical sample is case specific and one skilled in the art would readily be able to determine the quantity without undue experimentation.

The number of classes used to classify an object in accordance with embodiments of the present invention depends on a specific classification situation. For simplicity and to facilitate the discussion that follows, embodiments of the present invention will be described with reference to an example having only two groups or classes to which a measured object can be assigned. Thus, using this example, the multivariate estimation involves classifying a measured object as either being a member of a first class or a second class. For instance, the first class may be the class of "good" objects and the second class may be the class of "bad" objects (e.g., good solder joints and bad solder joints). However, the example using only two classes herein is not intended to limit the scope of the invention in any way. One skilled in the art can readily extend the discussion that follows to situations where there are more than two classes, such as the classes needed to define the different types of defects in bad solder joints, and still be within the scope of the present invention.

Continuing with the example of FIG. 3, once the setup process is completed for constructing a classifier from the training feature vectors $f_{T1}$–$f_{T6}$ for inspecting solder joints of a given type, such classifier is used for evaluating feature vectors associated with solder joints under inspection for classifying such solder joints as either "good" or "bad." More specifically, for each solder joint of a circuit board being presented for inspection, the inspection system measures features of such solder joint to determine a corresponding feature vector f. From the stored training feature vectors $f_{T1}$–$f_{T6}$, the inspection system determines the nearest k neighbors, i.e., the k features with the smallest Euclidean distance $((f-k)^T(f-k))^{1/2}$, where "T" is the matrix transpose. Using the convention that a vector can be treated as a column vector, the dot product of two vectors v and w can be written $v^T w$, as is well-known. Accordingly, the square of the Euclidean distance between two vectors f and k in the above example can be written ((f–k) dot (f–k)) or $((f-k)^T (f-k))$. The inspection system determines the labels (i.e., "good" or "bad") of these k nearest neighbors, and if most of them are "good," then the joint is determined to be "good", otherwise the joint is determined to be "bad."

For instance, in the example of FIG. 3, three solder joints are inspected by the inspection system, which determines feature vector $f_1$ for the first solder joint, feature vector $f_2$ for the second solder joint, and feature vector $f_3$ for the third solder joint. In determining whether each solder joint is acceptable, the inspection system determines whether the feature vector of such solder joint is sufficiently close to the "good" training feature vectors $f_{T1}$, $f_{T2}$, and $f_{T3}$. For instance, the first and second solder joints may be determined as being "good" in this example because their respective feature vectors $f_1$ and $f_2$ map relatively close to the "good" training feature vectors, while the third solder joint may be determined as being "bad" because its feature vector $f_3$ maps closer to the "bad" training feature vectors. Of course, such multivariate estimation determines the probability that a received feature vector (e.g., $f_1$, $f_2$, and $f_3$) is properly classified as a member of the "good" class and the probability that such received feature vector is properly classified as a member of the "bad" class, and based on the determined probabilities, the solder joint having the received feature vector may be assigned to the class to which it is most probably properly classified.

This inspection technique improves on the traditional inspection techniques in that it does not require a user to select thresholds (or boundaries) for each feature of an object under inspection. However, this inspection technique still has several disadvantages, including that it does not allow for consideration of risk management when inspecting objects (e.g., solder joints). For example, the accuracy of the k nearest neighbors method is sensitive to measurement noise in the feature vector f. This k nearest neighbors method is sensitive to noise because a point is generally classified like nearby points without taking into account: 1) the relative amount of influence each particular feature has on determining the class for a feature vector, and 2) how noisy each feature is. Noise in less valuable features can cause a feature vector to be closer to training vectors in the wrong class that to those in the correct class, for example. Additionally, the accuracy of the k nearest neighbors method is sensitive to elements of f that have low power for distinguishing between "good" and "bad" joints compared to elements of f. Further, this inspection technique does not allow for consideration of risk management. For instance, as described above, the cost of a false accept and of a false reject of a solder joint are not necessarily the same for a given product. This inspection technique does not take into account the relative cost of deciding that a good joint is bad ("false fail") versus deciding that a bad joint is good ("false accept").

Embodiments of the present invention provide a system and method for categorizing an object under inspection. For example, embodiments of the present invention are applicable for performing quality analysis of an object, such as a solder joint, to determine if such object is acceptable (classified as "good" versus "bad"). Further, embodiments of the present invention enable risk management considerations to be implemented within such quality analysis in a reliable and user-friendly manner. While a preferred embodiment is particularly applicable for classification of solder joints, embodiments of the present invention have much broader applicability and may, for example, be implemented for analyzing various other types of objects, as described further below. For example, an image of a solder joint may be processed to determine values of various features (or parameters) of such solder joint, thereby forming a feature vector value for such solder joint. Electrical connections are commonly formed between components using solder. However, various other techniques for making electrical connections are well known in the art, and even though example embodiments of the present invention are described herein in terms of solder joints, it should be understood that other types of electrical connections including, but not limited to, conductive epoxy, mechanical, tungsten and eutectic bonds, may be classified utilizing embodiments of the invention. Further, in certain implementations, an inspection system may be implemented at an airport, wherein an X-ray image of passenger baggage may be processed to determine values of various features of the contents of such baggage, thereby forming a feature vector for items within the baggage. Such feature vector may then be used to classify the contents of the baggage as either acceptable (e.g., safe for loading onto the airplane) or unacceptable (e.g., unsafe for loading onto the airplane).

Preferably, a classifier is constructed for the type of object under consideration (e.g., for a solder joint type) that is capable of receiving as input a given feature vector value for an object and determine the probability that such object is properly classified as being acceptable (or "good"). Further, a user-tunable cost (or risk) variable "K" may be used in determining whether the object having the determined probability of acceptability (as determined by the classifier) is worth accepting. Thus, a technician is not required to define the region of acceptable parameter values that takes into consideration the cost (or risk) associated with the product under study, but instead a defined classifier is used to determine a probability of acceptability, and the technician need only adjust (or tune) a risk variable to cause the inspection system to perform the desired type of analysis.

As described further below, a preferred embodiment of the present invention preferably combines dimension reduction, density estimation by cluster weighted modeling, Bayesian model selection, and Bayesian minimum error or minimum cost classification in order to construct a classifier for solder joint classification. It should be recognized that techniques, such as cluster weighted modeling, are well known for constructing a classifier based on a given set of training data, including as examples the techniques taught by K. Popat and R. W. Picard, "Cluster based probability model and its application to image and texture processing", *IEEE Trans. Image Processing*, 6(2):268–284, 1997, and N. Gershenfeld, B. Schoner, and E. Metois, "Cluster-weighted modeling for time-series analysis", *Nature*, vol. 397, pages 329–332, Jan. 28, 1999, the disclosures of which are hereby incorporated herein by reference. A further example of a preferred technique for constructing a classifier that may be used for determining whether an object under inspection (e.g., a solder joint) is a member of a particular class defined by such classifier is described in greater detail in co-pending and commonly assigned U.S. patent application Ser. No. 10/106,435 filed Mar. 26, 2002 entitled "METHOD AND SYSTEM OF OBJECT CLASSIFICATION EMPLOYING DIMENSION REDUCTION", the disclosure of which is hereby incorporated herein by reference.

Figure 4:
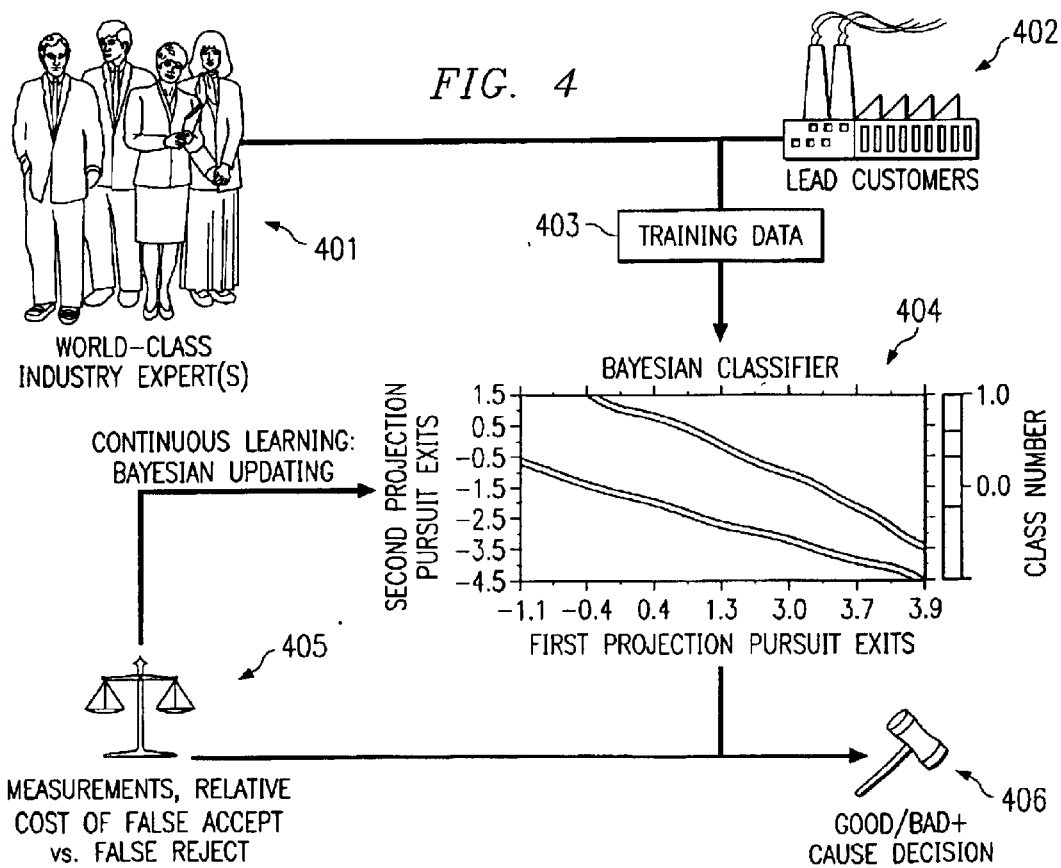
FIG. 4 shows an example overview of application of a preferred embodiment of the present invention.

Various embodiments of the present invention are now described with reference to FIGS. 4–11, wherein like reference numerals represent like parts throughout the several views. Turning first to FIG. 4, an example overview of application of a preferred embodiment of the present invention is shown. In a preferred embodiment, a classifier 404 is developed for a solder joint type, wherein such classifier is capable of specifying the probability that a solder joint of this type having a determined feature vector value is acceptable. For instance, training data 403 may be collected for various types of solder joints, such as J-lead, gullwing, and ball grid array (BGA) types of solder joints, as examples, from which a classifier 404 may be developed for each type of solder joint. More specifically, training data 403 may comprise data files containing a large number of feature vectors and "joint calls" (i.e., determinations whether the joint corresponding to the feature vector is truly considered good or bad), which may be obtained from X-ray inspection of solder joints produced by selected lead customers 402. The joint calls may be inspected and possibly corrected by an expert 401 in the technical field of solder joint quality. Experts 401 are available that are very knowledgeable in the field of solder joints, and many such experts 401 commonly lecture and educate others as to what constitutes a "good" quality solder joint for various different types of joints.

The result of obtaining such data from lead customers 402 and/or industry experts 401 is a quantity of training data 403 for each type of solder joint (e.g., J-lead, gullwing, ball grid array, etc.). These data may be written: $D=\{(f_1, c_1),(f_2, c_2), \ldots ,(f_{|D|}, c_{|D|})\}$, where here the indices indicate order within the set D and not element number within a vector, the $f_i$'s are feature vectors as described above, and $c_i \in \{good, bad\}$. The training data "D" 403 is preferably used to build classifier 404 in the manner described more fully below. Once classifier 404 is built, it is used to classify solder joints in a manner that is also further described below. More specifically, classifier 404 is preferably deployed in a solder joint inspection system to receive a feature vector value determined for a particular solder joint and determine a probability that such solder joint is acceptable.

Further, in a preferred embodiment, once the classifier 404 is deployed in such a joint inspection system, it may be tuned for a particular solder joint manufacturing process or manufacturing line by collecting additional feature vectors and joint calls $E=\{(f_j,c_j)\}$, setting $D \leftarrow D \cup E$, and re-executing the classifier construction method described further below. Thus "E" in the above equation is a set of additional feature vectors and calls that are obtained during operation of the manufacturing process or manufacturing line.

In a preferred embodiment, the classifier may further be tuned based on a received indication of risk 405 (e.g., relative cost of false accept versus false reject). For instance, as described in greater detail below, a preferred embodiment enables a technician to specify (as a cost variable "K") a relative cost of false acceptance of a solder joint versus false rejection of a solder joint in operational block 405, and such indication of risk is used by the inspection system in conjunction with the probability of acceptability determined by classifier 404 for a given solder joint to make a determination 406 as to whether the solder joint is acceptable. For example, classifier 404 may receive a feature vector value for a particular solder joint being analyzed and may compute a probability that such solder joint is acceptable (e.g., 85% probability that such solder joint is acceptable), and the inspection system may use a relative cost variable 405 to determine in operational block 406 whether the solder joint having the determined probability of acceptability is worth accepting (i.e., whether it is cost-effective to accept the solder joint).

Figure 5:
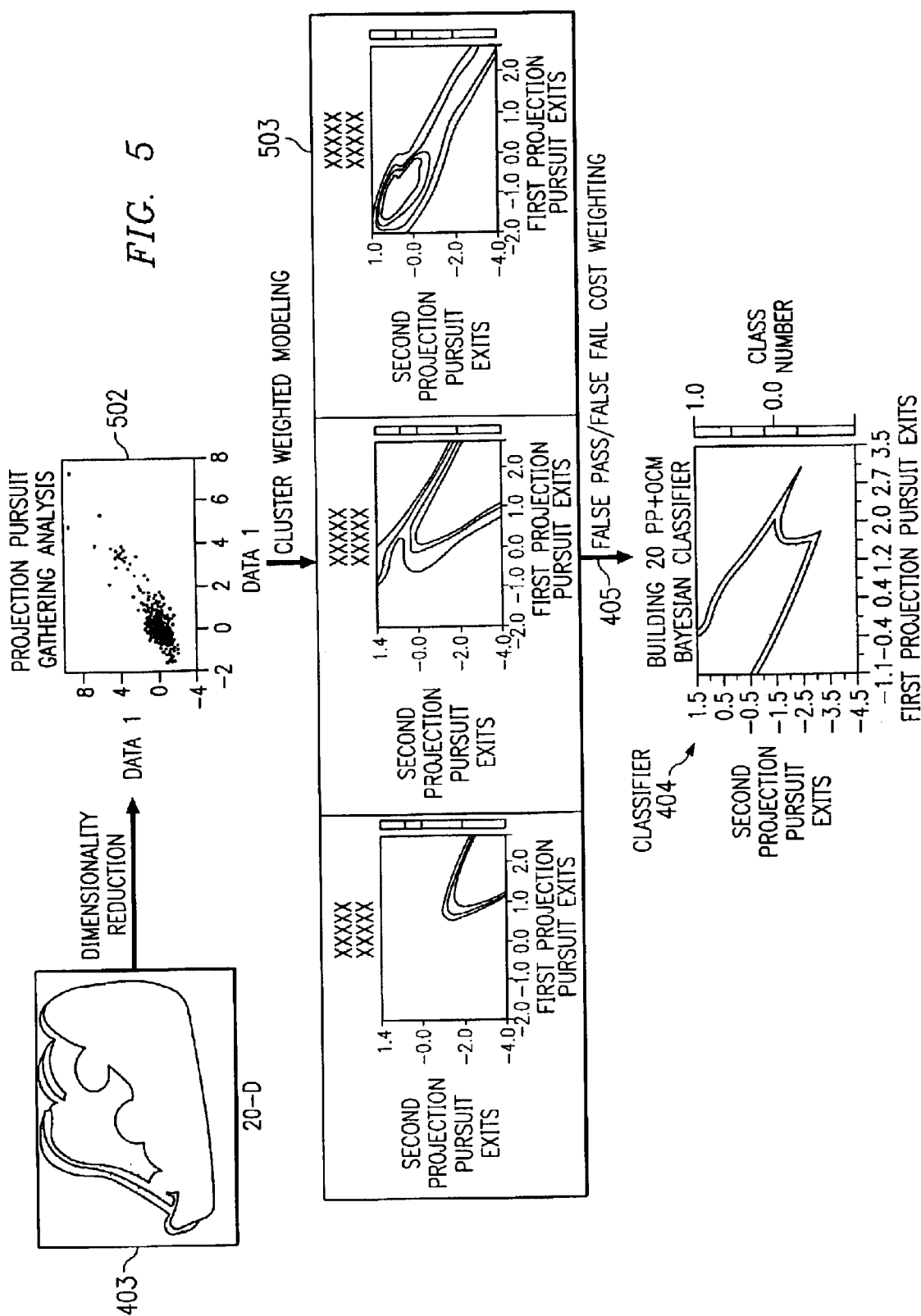
FIG. 5 shows an example technique for constructing a classifier in accordance with a preferred embodiment of the present invention.

Turning now to FIG. 5, an example technique for constructing classifier 404 in accordance with a preferred embodiment of the present invention is shown. As shown, training data 403 is preferably utilized in construction of classifier 404. More specifically, the construction process utilizes the following inputs: D (which is defined above), minimum number of clusters $M_{min}$, maximum number of clusters $M_{max}$, and it utilizes the following outputs: shift vector $\mu$, scaling vector s, dimension reduction matrix R, cluster weighted model CW M. These inputs and outputs are described further below.

Preferably, a reduced dimension space is determined that maximally separates good and bad joints' feature vectors. Preferably, the method disclosed in U.S. patent application Ser. No. 10/106,435 filed Mar. 26, 2002 entitled "METHOD AND SYSTEM OF OBJECT CLASSIFICATION EMPLOYING DIMENSION REDUCTION" (the disclosure of which is hereby incorporated herein by reference) is applied to D, thus yielding shift vector $\mu$, scaling vector s, and dimension reduction matrix R. Thereafter, from the training data 403, a reduced dimension data set 502 is computed. That is, the reduced dimension data set $\hat{D}=\{(\hat{f}_i, c_i)\}$ is computed from D, in which the following transformation is applied to each feature vector $f_i$ in D:

$$\hat{f}_i = R \, \text{diag}(s)^{-1}(f_i - \mu),$$ where diag (.) constructs a diagonal matrix from a vector, i.e., $$\text{diag}(x)_{kl} = \begin{cases} x_k & \text{if } k = l \\ 0 & \text{otherwise} \end{cases}.$$

Preferably, a portion of the original data set D is reserved for validation. For example, let $N=\lfloor(1-v)|D|\rfloor$, where $0<v<1$ (preferably, $v=0.25$ if there are no other considerations). This portion of data set D is used for validation by applying the data to the model and checking to see how often the classification results correspond to the known calls. This allows an estimate of the classification accuracy to be projected.

Thereafter, cluster weighted modeling is performed to generate cluster weighted models 503. For instance, in a preferred embodiment, for each cluster M in $M_{min} \leq M < M_{max}$ the following is performed:

(a) Construct a cluster-weighted model with M clusters:

i. Set $\vec{x} = (f_1, f_2, \ldots f_N)$ ii. Set $\vec{s} = (c_1, c_2, \ldots, c_N)$.

iii. Apply the discrete observables variant of cluster-weighted modeling expectation maximization, in the manner as described in greater detail by Neil Gershenfeld in *The Nature of Mathematical Modeling* at pages 178–185 (Cambridge University Press, 1999) (the disclosure of which is incorporated herein by reference), thus yielding the cluster weighted model:

$$CWM_M = (\{c_m\}_{m=1}^M, \{\mu_m\}_{m=1}^M, \{C_m\}_{m=1}^M, \{p(s|x, c_m)\}_{m=1}^M).$$

(b) Compute the posterior log likelihood L(M) of the validation data given the cluster weighted model $CWM_M$, in the manner as follows:

i. For each i where $N < i \leq |D|$, let $x_i = \hat{f}_i$ and $s_i = c_i$. Compute $p(s_i|x_i)$ as described in greater detail by Neil Gershenfeld in *The Nature of Mathematical Modeling* (e.g., in accordance with Equation 14.38 provided therein).

ii. Compute the posterior log likelihood of the validation data with M clusters, i.e., L(M), as follows:

$$L(M) = \sum_{i=N+1}^{|D|} \log p(s_i | x_i).$$

Thereafter, the best model is selected for use in the solder joint inspection system. For example, in a preferred embodiment, the best model, $M_{best}$, is determined as being the first local maximum of the posterior log likelihood of the validation data. That is, $M_{best}$, least such that $M_{min} \leq M_{best} < M_{max}$, and $L(M_{best}) > L(M_{best-1})$ and $L(M_{best}) > L(M_{best+1})$, where for convenience consider $M_{min-1} = M_{max} = \infty$. Then, the cluster weighted model to be used is set as the determined best cluster weighted model (i.e., CW M=CW M ($M_{best}$)).

An alternative method is to divide the reduced dimension data 502 into two sets: 1) a set of feature vectors of good joints, and 2) a set of feature vectors of bad joints. Then, a density estimate using expectation maximization (EM) may be performed on each set independently, in the manner as described in greater detail by Neil Gershenfeld in *The Nature of Mathematical Modeling* at pages 172–178 (Cambridge University Press, 1999). This alternative method would involve determining the number of clusters needed to represent the density of the good and bad joints separately. Thus, twice as many candidate models would have to be created and two best models selected (one best model for good joints and one best model for bad joints). The resulting algorithm of this alternative method would likely run slower and perhaps be less reliable than the above-described method of a preferred embodiment.

Preferably, classifier 404, once constructed, may receive a cost weighting variable 405 (also referred to herein as cost weighting variable "K") as an input to determine whether a solder joint is acceptable. It should be recognized that any techniques now known or later developed for constructing a classifier that is operable to receive a feature vector and determine a probability that such feature vector is properly assigned membership within one of a plurality of different classes may be utilized, including without limitation the construction technique disclosed in U.S. patent application Ser. No. 10/106,435 filed Mar. 26, 2002 entitled "METHOD AND SYSTEM OF OBJECT CLASSIFICATION EMPLOYING DIMENSION REDUCTION" (the disclosure of which is hereby incorporated herein by reference). Thus, the scope of the present invention is not limited to any particular classifier construction technique. As described further below, the constructed classifier of embodiments of the present invention is implemented so as to receive at least a feature vector f for an object to be classified and a cost variable "K". Thus, techniques now known or later discovered for constructing a classifier may be modified to allow for a constructed classifier to receive a cost variable "K" in the manner described further below. That is, in addition to a classifier computing the probability that an object having a given feature vector f is properly classified within a particular class (e.g., the probability that an object is properly classified as "good"), the classifier is also implemented to use a cost variable "K" to determine, given the computed probability, the most cost-effective classification to assign the object.

Figure 6:
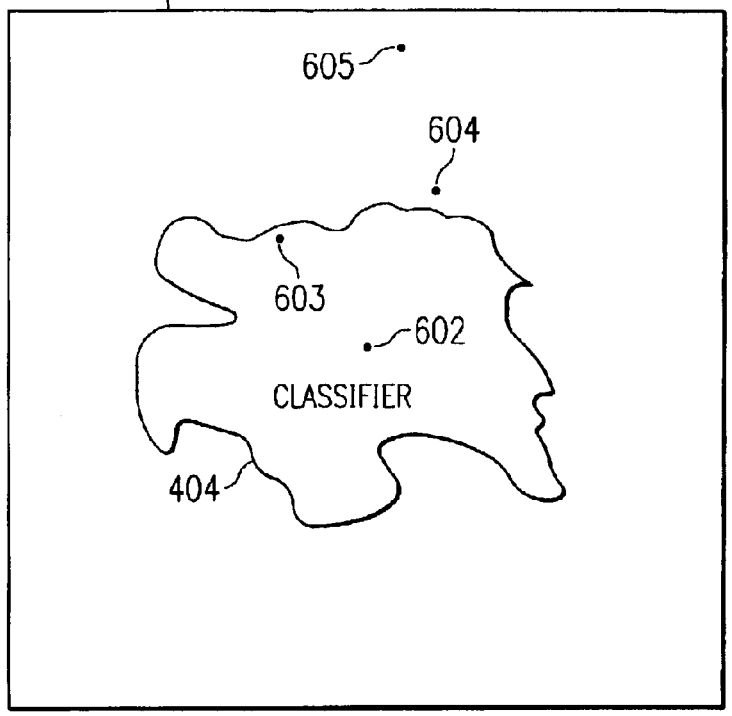
FIG. 6 shows an example representation of a classifier defined in accordance with a preferred embodiment of the present invention.

Turning to FIG. 6, an example of a classifier 404 defined in accordance with a preferred embodiment of the present invention is illustrated. In the example of FIG. 6, feature space 601 represents all possible values of a feature vector f for a solder joint. Within such feature space 601, classifier 404 defines a region of feature vector values that indicate their respective solder joint is of acceptable quality. During the quality analysis process, a solder joint is considered "good" if its feature vector lies within the classifier 404. While FIG. 6 provides a two-dimensional example (i.e., two parameters are used for measuring the quality of a solder joint) for ease of illustration, such quality analysis usually utilizes many more parameters (resulting in "N"-dimension space for graphically representing the acceptable region).

As described further below, in a preferred embodiment, such classifier 404 may be tuned for desired risk management based on the value assigned to cost variable "K." Thus, for instance, a classifier 404 may be constructed for a given type of solder joint, such as a BGA joint, and if an electronic product (e.g., a circuit board) under inspection includes BGA solder joints, then classifier 404 may be invoked for inspecting such BGA solder joints (and other classifiers may be available for use in inspecting other types of solder joints). However, the relative cost variable for the classification process may vary depending on the product being inspected, which may result in tuning classifier 404 as desired. For instance, if the product being inspected is a high-end product (e.g., is destined for a satellite), then it may be much more costly to have a truly bad BGA joint classified as "good" than to have a truly good BGA joint classified as "bad." Accordingly, for inspection of such product a proper cost variable "K" may be input to the classifier to tune the classifier 404 for performing cost-effective classification of BGA joints in such product (e.g., to ensure a high probability of a joint being "good" before classifying such joint as "good"). On the other hand, if the product being inspected is a low-cost product (e.g., a low-cost consumer product that is destined for a retailer), then it may be much less costly to have a truly bad BGA joint classified as "good" than to have a truly good BGA joint classified as "bad." Accordingly, for inspection of such product a proper cost variable "K" may be input to the classifier to tune the classifier 404 for performing cost-effective classification of BGA joints in such low-cost product (e.g., to require a lower probability of a joint being "good" before classifying such joint as "good"). It should be recognized that classifier 404 may be used in classifying BGA joints irrespective of the product in which the joints are implemented, and cost variable "K" may fine-tune the classifier 404 in accordance with the risk management considerations associated with a given product under inspection.

In embodiments of the present invention, at least a feature vector f and a cost variable K are input to a classifier for classifying an object under inspection. The classifier uses these inputs to determine the classification of the object having the received feature vector f. In certain embodiments, various other inputs may also be supplied to the classifier and may also be used in classifying the object under inspection. In a preferred embodiment, classifier 404 receives the following inputs in addition to a feature vector f and a cost variable K: a cluster weighted model (e.g., CWM computed as described above), a dimension reduction matrix R, a scaling vector s, and a shift vector $\mu$.

In a preferred embodiment, a user (e.g., a technician) may specify a cost weighting variable (or "risk" variable) "K" that is taken into consideration when classifying the solder joint under inspection. For example, given the probability of acceptability (i.e., the probability of the solder joint having a given feature vector f as being "good") determined by a classifier for the solder joint type, a cost weighting variable "K" implemented for this particular inspection process may be utilized by the classifier in determining whether it is cost-effective to accept such solder joint (i.e., to classify it as "good"). As described above, the classifier receives at least two inputs: 1) a feature vector f extracted from an image of the solder joint under study, and 2) a relative cost K of an incorrect fail decision versus an incorrect false accept decision. That is, $$K = \frac{Cost\_of\_Determining\_a\_Good\_Joint\_as\_Being\_Bad}{Cost\_of\_Determining\_a\_Bad\_Joint\_as\_Being\_Good}.$$

The value of K need not be known exactly for this classification method to be advantageously used. For instance, having an estimate of K correct in order of magnitude will be good enough in practice. If instead of the cost of wrong decisions being minimized it is desired to minimize the number of wrong decisions, the value K=1 may be selected in a preferred embodiment. It should be noted that in the above example K will be larger for products for which higher quality is required (e.g., a product destined for a satellite) than for products in which high quality is not as valuable (e.g., inexpensive products destined for a retail store).

Figure 7:
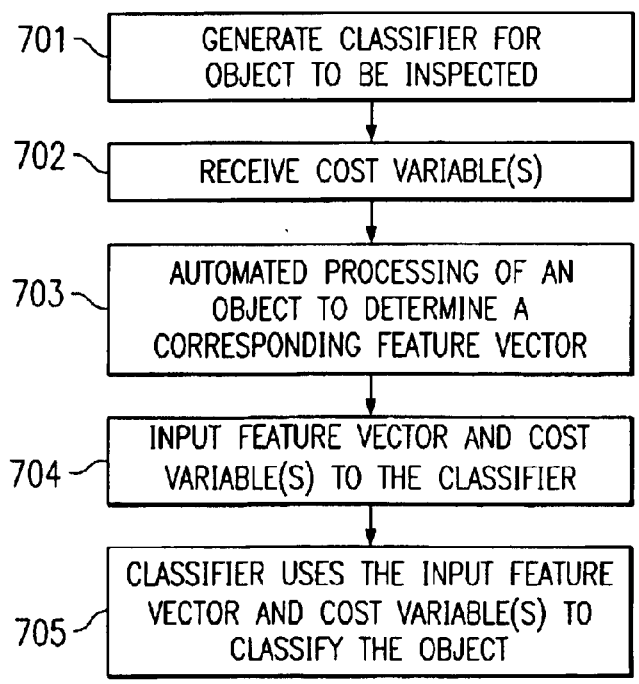
FIG. 7 shows an example operational flow diagram for embodiments of the present invention.

Turning now to FIG. 7, an example operational flow diagram for embodiments of the present invention is shown. As shown, a classifier, such as classifier 404 described above, for an object to be studied (e.g., solder joint type, items in luggage being inspected, or other object) is generated (or "constructed") in operational block 701. As described above, such classifier is preferably generated based at least in part on training data, which may comprise various feature vector values for the type of object under study and a corresponding indication for each of the feature vector values as to its proper classification. In operational block 702, the cost variable(s) (e.g., cost variable K) is received. Such cost variable(s) preferably indicate the relative "cost" (or "risk") associated with the inspection system incorrectly classifying an object (e.g., identifying a good object as being bad and vice-versa). As described above, the cost variable K may vary depending on the risk management concerns associated with a particular product under inspection, which may in turn tune the classification process accordingly. For instance, a first value of K may be used when inspecting a high-end product, whereas a different value of K may be used when inspecting a low-end product.

In operational block 703, the object being inspected undergoes automated processing to determine a corresponding feature vector f for such object. For example, an object, such as a solder joint, may undergo image processing (e.g., laminography) to determine a feature vector f that corresponds to values for various features (or parameters) of the object. Thereafter, in operational block 704, the received cost variable(s) and the computed feature vector f are input to the classifier for the object being inspected (e.g., a classifier for the particular type of solder joint being inspected). Then, in operational block 705, the classifier uses the cost variable(s) K and feature vector f to determine a cost-effective classification of the object (e.g., to determine whether it is cost-effective to classify the solder joint as "good").

Figure 8:
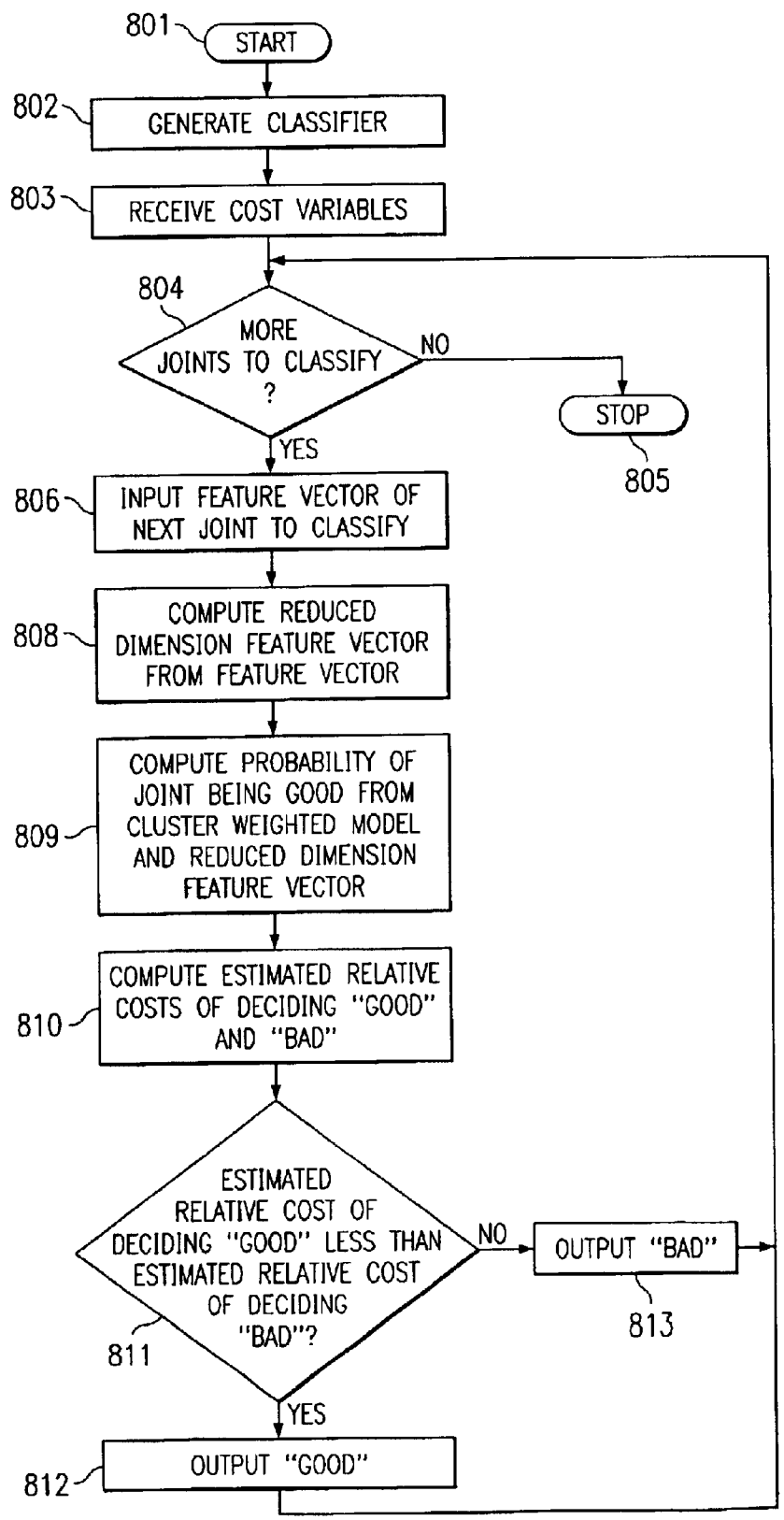
FIG. 8 shows an example operational flow for a preferred embodiment for classifying a solder joint under inspection as either "good" or "bad"

FIG. 8 shows an example operational flow for a preferred embodiment for classifying a solder joint under inspection as either "good" or "bad." Operation begins in operational block 801. In operational block 802, a classifier is constructed for the solder joint type to be inspected (e.g., a BGA type of solder joint). It should be understood that such classifier need not always be constructed for each inspection process. For instance, if a classifier for the solder joint type (e.g., a classifier for BGA solder joints) were previously constructed, it may be utilized in this inspection process, as opposed to re-constructing the classifier. In operational block 803, cost variable K is received. As described above, such cost variable may depend on the risk management concerns associated with the particular product in which the solder joint under inspection is implemented. The cost variable K effectively tunes the classification process performed by the classifier in accordance with the risk management concerns.

Operational blocks 802 and 803 may be performed at the outset of the inspection process. Thereafter, the classifier received/constructed in block 802 and the cost variable K received in block 803 are used to inspect solder joints. For instance, in operational block 804 it is determined whether there are more solder joints to be classified. Once it is determined that no further solder joints are to be classified, then the process may end at block 805. However, if there are further solder joints to be classified, then the process advances to block 806 whereat a feature vector f of the next solder joint to be classified is received as input to the classifier. In a preferred embodiment, the classifier computes, in block 808, a reduced dimension feature vector corresponding to received feature vector f: $\hat{f}=R\text{diag}(s)^{-1}(f-\mu)$.

The classifier then, in block 809, uses the cluster weighted model CWM (e.g., CWM 503 of FIG. 5) to compute the probability that the reduced dimension feature vector (and hence f) corresponds to a "good" joint. Preferably, such probability may be computed as follows: Let x=$\hat{f}$, s=good, and compute p(s|x) according to Equation 14.38 described by Neil Gershenfeld in *The Nature of Mathematical Modeling* at pages 172–178 (Cambridge University Press, 1999) (the disclosure of which is incorporated herein by reference). Of course, in alternative embodiments, other techniques now known or later discovered for determining the probability that a feature vector corresponds to a "good" joint may be used in the classifier.

Further, in alternative embodiments, a reduced dimension feature vector corresponding to a received feature vector f may not be computed (e.g., block 808 may be eliminated), but instead the received feature vector f itself may be used in determining the probability that its respective joint is "good." Thus, unless otherwise specified herein, when referring to a classifier using a feature vector f for computing the probability that the object to which such feature vector relates (e.g., a solder joint) is properly classified in a given classification (e.g., "good"), it is to be understood that such feature vector f is intended to encompass use of either the exact feature vector f that is received by the classifier as well as use of a reduced dimension feature vector corresponding to the received feature vector.

Thereafter, for the specified cost variable "K", the estimated relative costs associated with classifying a solder joint as being "good" and the estimated relative costs associated with classifying the solder joint as being "bad" are determined, in block 810. That is, the expected relative costs of each decision is computed, such as follows:

(a) $E[RC(\text{good})]=1 \cdot (1-p(\text{good}|x))=1-p(\text{good}|x)$; and (b) $E[RC(\text{bad})]=K \cdot (1-p(\text{bad}|x))=K \cdot p(\text{good}|x)$.

In the above "E[RC(good)]" is the estimated relative cost associated with classifying a solder joint as "good" and "E[RC(bad)]" is the estimated relative cost associated with classifying a solder joint as "bad." Given the above determinations, the least expensive cost decision may be made in determining whether the solder joint under consideration is of acceptable quality. That is, it is determined in block 811 whether $E[RC(\text{good})] \leq E[RC(\text{bad})]$. If it is determined in block 811 that $E[RC(\text{good})] \leq E[RC(\text{bad})]$, then the classifier assigns the solder joint under inspection to class "good" in block 812. That is, the classifier determines that it is cost-effective to classify the solder joint as "good" in block 812. Otherwise, the classifier assigns the solder joint under inspection to class "bad" in block 813. That is, the classifier determines that it is cost-effective to classify the solder joint as "bad" in block 813. In either case, operation then returns to block 804 to determine whether there are further solder joints to classify. Of course, rather than computing the cost variable K for each solder joint in products of a particular type (as in this example of FIG. 8), the cost variable K may be computed and set for an entire product run, and may vary depending on the particular product being manufactured. That is, the cost variable K may be determined for a particular type of product, and it may be used in inspecting all solder joints of that particular type of product, as opposed to computing the cost variable K for each solder joint of the particular type of product.

Figure 9:
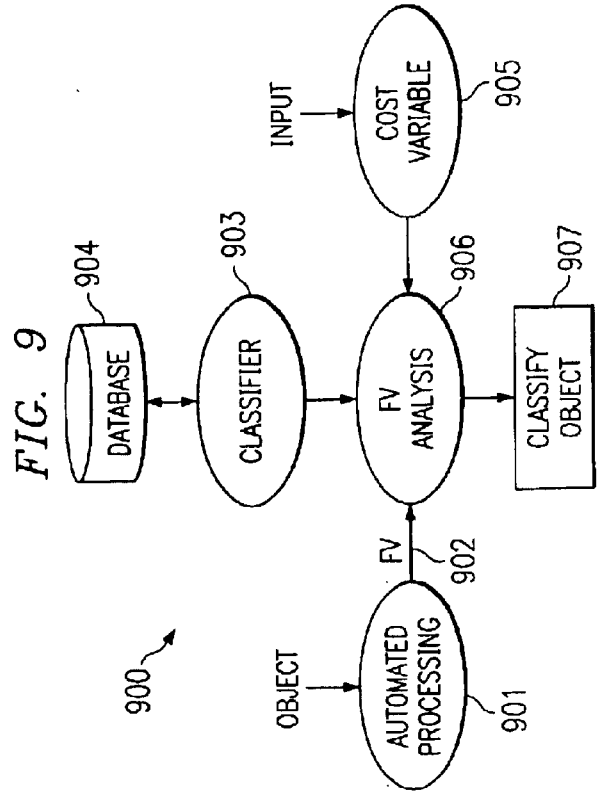
FIG. 9 shows a functional block diagram of an example classification system in which embodiments of the present invention may be implemented.

Turning now to FIG. 9, an example overview of a classification system 900 (e.g., an automated inspection system) in which embodiments of the present invention may be implemented is shown as a functional block diagram. As shown, system 900 comprises an automated processing system 901 (e.g., an image processing system, such as a laminography system) that is operable to process an object and generate a feature vector f 902. Such feature vector f 902 is input to a feature vector analysis system 906 that is operable to use classifier 903 and cost variable 905 to analyze the received feature vector and classify its corresponding object (shown as output 907). As described above, classifier 903 may be constructed from training data stored in a database 904. As further described above, cost variable K 905 may be input from a user (e.g., technician) and may be used to tune classifier 903 for risk management concerns.

Figure 10:
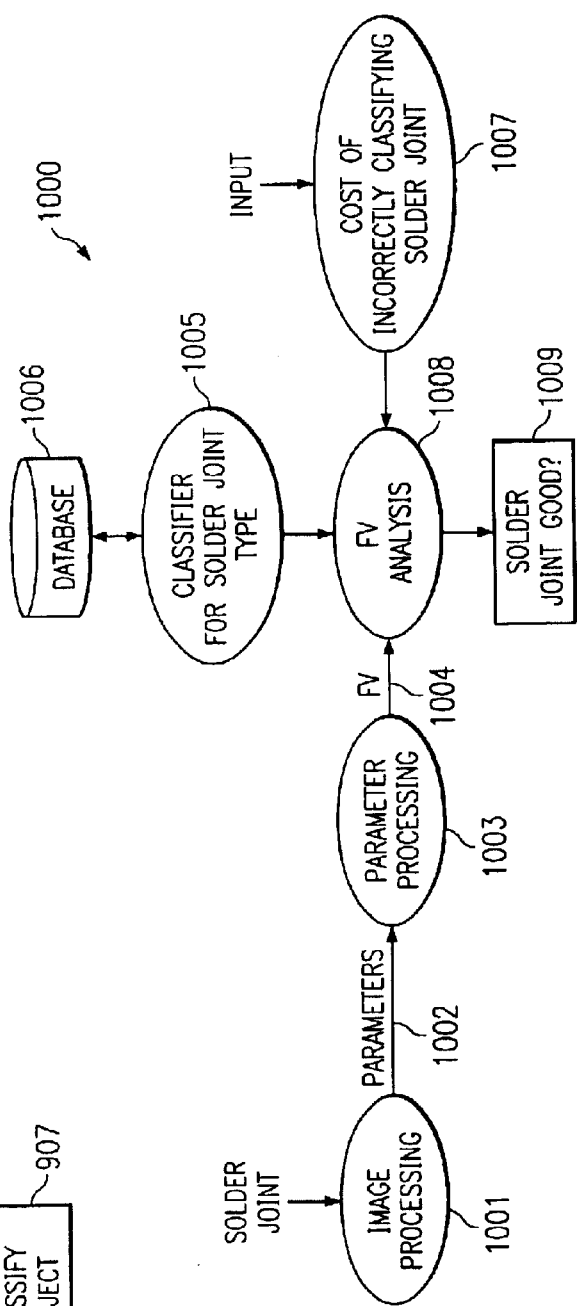
FIG. 10 shows a functional block diagram of a more specific example of an inspection system for inspecting a solder joint in which embodiments of the present invention may be implemented.

FIG. 10 shows a functional block diagram of a more specific example of an inspection system 1000 for inspecting a solder joint in which embodiments of the present invention may be implemented. As shown, system 1000 comprises an image processing system 1001 (e.g., a laminography system) that is operable to capture an image of a solder joint under inspection. Parameters (or "features") 1002 of the solder joint, such as length, width, thickness, etc., that are obtained from such image processing are input to parameter processing block 1003, which processes parameters 1002 to construct a feature vector f 1004. Such feature vector f 1004 is input to a feature vector analysis system 1008 that is operable to use a classifier 1005 for the type of solder joint under inspection and cost variable 1007 for the inspection process (which may depend on the product being inspected) to analyze the received feature vector 1004 and classify its corresponding solder joint as either "good" or "bad" (shown as output 1009). As described above, classifier 1005 may be constructed from training data stored in a database 1006. As further described above, cost variable K 1007 may be input from a user (e.g., technician) and may be used to tune classifier 1005 for risk management concerns.

When implemented via computer-executable instructions, various elements of embodiments of the present invention are in essence the software code defining the operations of such various elements. The executable instructions or software code may be obtained from a readable medium (e.g., a hard drive media, optical media, EPROM, EEPROM, tape media, cartridge media, flash memory, ROM, memory stick, and/or the like) or communicated via a data signal from a communication medium (e.g., the Internet). In fact, readable media can include any medium that can store or transfer information.

Figure 11:
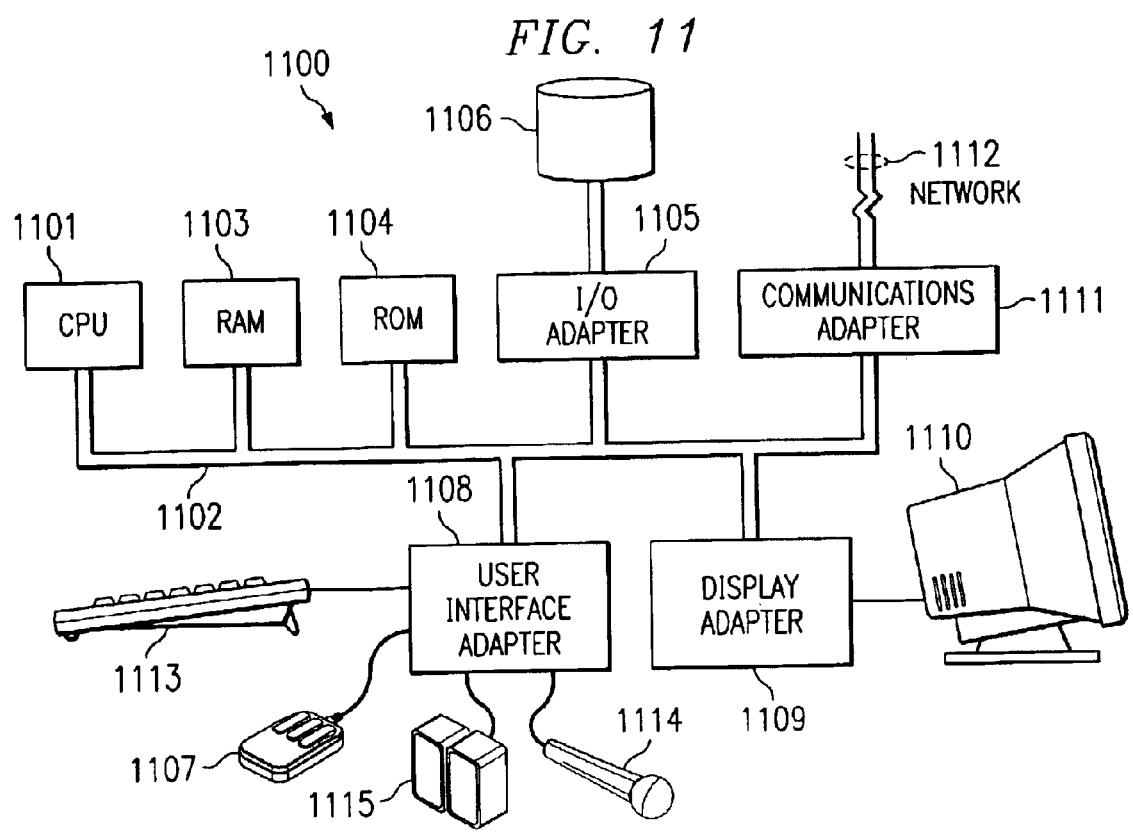
FIG. 11 shows an example computer system on which embodiments of the present invention may be implemented.

FIG. 11 illustrates an example computer system 1100 adapted according to embodiments of the present invention. That is, computer system 1100 comprises an example system on which embodiments of the present invention may be implemented. Central processing unit (CPU) 1101 is coupled to system bus 1102. CPU 1101 may be any general purpose CPU. Suitable processors include without limitation any processor from HEWLET-PACKARD's ITANIUM family of processors, HEWLETT-PACKARD's PA-8500 processor, or INTEL's PENTIUM® 4 processor, as examples. However, the present invention is not restricted by the architecture of CPU 1101 as long as CPU 1101 supports the inventive operations as described herein. Further, in certain embodiments, computer system 1100 may comprise a plurality of CPUs 1101 (e.g., may be a multi-processor system, as is well known in the art). CPU 1101 may execute the various logical instructions according to embodiments of the present invention. For example, CPU 1101 may execute machine-level instructions according to the exemplary operational flows described above in conjunction with FIGS. 7 and 8.

Computer system 1100 also preferably includes random access memory (RAM) 1103, which may be SRAM, DRAM, SDRAM, or the like. Computer system 1100 preferably includes read-only memory (ROM) 1104 which may be PROM, EPROM, EEPROM, or the like. RAM 1103 and ROM 1104 hold user and system data and programs, as is well known in the art.

Computer system 1100 also preferably includes input/output (I/O) adapter 1105, communications adapter 1111, user interface adapter 1108, and display adapter 1109. I/O adapter 1105, user interface adapter 1108, and/or communications adapter 1111 may, in certain embodiments, enable a user to interact with computer system 1100 in order to input information, such as cost variable K described above and/or training data for constructing a classifier.

I/O adapter 1105 preferably connects to storage device(s) 1106, such as one or more of hard drive, compact disc (CD) drive, floppy disk drive, tape drive, etc. to computer system 100. The storage devices may be utilized when RAM 1103 is insufficient for the memory requirements associated with storing data for constructing a classifier and/or classifying an object under inspection. Communications adapter 1111 is preferably adapted to couple computer system 1100 to network 1112. User interface adapter 1108 couples user input devices, such as keyboard 1113, pointing device 1107, and microphone 1114 and/or output devices, such as speaker (s) 1115 to computer system 1100. Display adapter 1109 is driven by CPU 1101 to control the display on display device 1110 to display information to a user such as, for example, the classification of an object under inspection.

It shall be appreciated that the present invention is not limited to the architecture of system 1100. For example, any suitable processor-based device may be utilized, including without limitation personal computers, laptop computers, computer workstations, and multi-processor servers. Moreover, embodiments of the present invention may be implemented on application specific integrated circuits (ASICs) or very large scale integrated (VLSI) circuits. In fact, persons of ordinary skill in the art may utilize any number of suitable structures capable of executing logical operations according to the embodiments of the present invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims arc intended to include within their scope such processes, machines, manufacture, compositions of matter, means, methods, or steps.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for classifying an object as being a member of one of a plurality of classes, the method comprising:

computing a probability that an object under inspection is properly assigned membership in a first of a plurality of classes; and using a cost variable to determine whether it is cost-effective to assign the object to said first of said plurality of classes given the computed probability.

2. The method of claim 1 wherein said object under inspection comprises a solder joint.

3. The method of claim 1 wherein said plurality of classes comprises a good class for objects that meet a pre-defined criteria and a bad class for objects that do not meet said pre-defined criteria.

4. The method of claim 3 wherein said first of said plurality of classes comprises said good class.

5. The method of claim 3 wherein said cost variable comprises a variable $$K = \frac{C_{GB}}{C_{BG}},$$

wherein $C_{GB}$ is a cost associated with incorrectly classifying a good object as bad and $C_{BG}$ is a cost associated with incorrectly classifying a bad object as good.

6. A method for classifying an object under inspection, said method comprising:

inputting a feature vector for an object under inspection to a classifier for said object;

inputting a cost variable to said classifier that specifies a cost associated with incorrectly classifying said object under inspection in a first of a plurality of classes;

said classifier using said feature vector to compute a probability that said object under inspection is properly assigned membership in said first of a plurality of classes; and said classifier using said cost variable to determine whether it is cost-effective to assign the object to said first of said plurality of classes given the computed probability.

7. The method of claim 6 wherein said object under inspection comprises a solder joint.

8. The method of claim 6 wherein said plurality of classes comprises a good class for objects that meet a pre-defined criteria and a bad class for objects that do not meet said pre-defined criteria.

9. The method of claim 8 wherein said cost variable comprises a variable $$K = \frac{C_{GB}}{C_{BG}},$$

wherein $C_{GB}$ is a cost associated with incorrectly classifying a good object as bad and $C_{BG}$ is a cost associated with incorrectly classifying a bad object as good.

10. A method for inspecting an object, said method comprising:

constructing a classifier for a first type of object that is operable to compute for an object of said first type that is under inspection a probability that such object under inspection is properly assigned membership in a first of a plurality of different classes; and inputting a cost variable to said classifier to tune said classifier for cost-effective classification of said object of said first type that is under inspection.

11. The method of claim 10 wherein said cost variable specifies a cost associated with incorrectly classifying said object of said first type that is under inspection in said first of a plurality of classes.

12. The method of claim 10 further comprising:

using the cost variable to compute, for each of the plurality of different classes, a cost associated with assigning the object under inspection to the respective class based at least in part on the determined probability that such object is properly assigned membership in the respective class; and determining the most cost-effective one of the plurality of different classes to which to assign the object under inspection based at least in part on the computed costs associated with each of the plurality of different classes.

13. The method of claim 10 wherein said first type of object comprises a first type of solder joint.

14. The method of claim 13 wherein said first type of solder joint comprises one selected from the group consisting of:

J-lead solder joint, gullwing solder joint, and ball grid array (BGA) solder joint.

15. The method of claim 10 wherein said first type of object comprises a first type of electrical connection.

16. The method of claim 15 wherein said first type of electrical connection comprises one selected from the group consisting of:

solder joint, conductive epoxy, mechanical bond, tungsten bond, and eutectic bond.

17. A system for classifying an object under inspection, said system comprising:

at least one processor; and computer-executable code stored to a computer-readable medium, said computer-executable code executable by said at least one processor to receive a feature vector for an object under inspection, receive a cost variable that specifies a cost associated with incorrectly classifying said object under inspection, use said feature vector to compute, for each of a plurality of classes, a probability that said object under inspection is properly assigned membership in the respective class, and use said cost variable to determine the most cost-effective one of the plurality of classes to which to assign the object given the computed probability of each of the plurality of classes.

18. The system of claim 17 wherein said computer-executable code executable to use said cost variable to determine the most cost-effective one of the plurality of classes comprises:

computer-executable code executable to use the cost variable to compute, for each of the plurality of different classes, a cost associated with assigning the object under inspection to the respective class based at least in part on the computed probability that such object is properly assigned membership in the respective class; and computer-executable software code executable to determine the least costly one of the plurality of different classes to which to assign the object under inspection.

19. The system of claim 17 further comprising:

input means for inputting said cost variable to said system.

20. The system of claim 17 further comprising an image processing means for generating said feature vector from at least one image of said object under inspection.

21. The system of claim 17 wherein said object under inspection comprises a solder joint.

* * * * *